United States Patent [19]

Stapp

[11] 4,075,412
[45] Feb. 21, 1978

[54] PROCESSES FOR PREPARATION OF DIACYLOXY OLEFINS

[75] Inventor: Paul R. Stapp, Bartlesville, Okla.

[73] Assignee: Phillips Petroleum Company, Bartlesville, Okla.

[21] Appl. No.: 678,856

[22] Filed: Apr. 21, 1976

[51] Int. Cl.² ............................................. C07C 67/05
[52] U.S. Cl. ................................ 560/244; 260/410.6; 260/464; 260/465 D; 260/465.4; 560/1; 560/89; 560/112; 560/127; 560/198; 560/230
[58] Field of Search .......... 260/497 R, 476 R, 465 D, 260/464, 465.4, 468 R, 468, 475 N, 485 N, 487, 410.6

[56] References Cited

U.S. PATENT DOCUMENTS

| 2,092,295 | 9/1937 | Paski | 260/2 |
| 2,093,695 | 9/1937 | Larson | 260/106 |
| 2,414,999 | 1/1947 | Bearse | 260/497 |

Primary Examiner—James O. Thomas, Jr.
Assistant Examiner—Michael Shippen

[57] ABSTRACT

Diacyloxy olefins are prepared by the reaction of a conjugated diolefin with a carboxylic acid in the presence of free oxygen and a catalyst system consisting essentially of an indium compound, a halide source and an alkali metal compound.

8 Claims, No Drawings

PROCESSES FOR PREPARATION OF DIACYLOXY OLEFINS

This invention relates to a process for the production of unsaturated diesters.

Various methods for the production of unsaturated diesters are known in the art.

It is an object of this invention to provide a novel process for the production of unsaturated diesters.

Other objects, aspects and advantages of this invention will be readily apparent to those skilled in the art from the reading of the following disclosure.

In accordance with the present invention there is provided a process for the production of unsaturated diesters which comprises contacting a mixture of a conjugated diolefin, a carboxylic acid and free oxygen with a catalyst system consisting essentially of an indium compound, a halide source and an alkali metal compound under reaction conditions.

The conjugated diolefin is selected from the group consisting of acyclic conjugated diolefins having from 4 to 16 carbon atoms per molecule and corresponding to the general formula

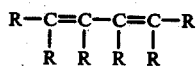

and cyclic conjugated diolefins having from 5 to 16 carbon atoms per molecule and corresponding to the general formula

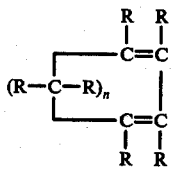

wherein, in each of the above formulas, R can be hydrogen, halogen, cyano, —COOR' or a hydrocarbyl radical containing up to 12 carbon atoms selected from the group consisting of alkyl, aryl, cycloalkyl and combinations thereof, such as aralkyl, alkaryl and the like. R' can be hydrogen or an alkyl radical of up to 10 carbon atoms or an aryl radical of up to 10 carbon atoms. The integer $n$ can range from 1 to 12.

Examples of suitable conjugated diolefins include: 1,3-butadiene, 2-methyl-1,3-butadiene, 2-chloro-1,3-butadiene, 2-ethyl-1,3-butadiene, 2-chloro-3-methyl-1,3-butadiene, 1,3-cyclohexadiene, 1,3-cyclooctadiene, 1,3-cyclododecadiene, 2-cyano-1,3-butadiene, 5-methyl-1,3-cyclohexadiene, 2,4-cyclohexadiene-1,2-dicarboxylic acid, octafluoro-1,3-cyclohexadiene, hexachloropentadiene, 5,6,7,8-tetrabromo-1,3-cyclooctadiene, 2-cyclohexyl-1,3-butadiene, 2-methylene-3-butenoic acid, 2,4-pentadienenitrile, cyclopentadiene, 2-carbethoxy-1,3-butadiene, and the like.

In a presently preferred embodiment the conjugated diolefins employed in the process of this invention are those which contain only carbon and hydrogen.

The carboxylic acid is selected from the group consisting of monocarboxylic acids having from 2 to 18 carbon atoms per molecule characterized by the general formula

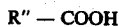

and dicarboxylic acids having from 2 to 18 carbon atoms per molecule characterized by the formula

wherein R" is selected from the group consisting of alkyl, cycloalkyl and aryl radicals and halogen, cyano and —COOR' substituted derivatives thereof, wherein up to four halogen, cyano or —COOR' substituents can be present in the R" group; and wherein R''' is selected from the group consisting of a valence bond and alkylene, cycloalkylene and arylene radicals and halogen, cyano and —COOR' substituted derivatives thereof, wherein up to four halogen, cyano or —COOR' substituents can be present in the R''' group. R' has been previously defined.

Examples of suitable carboxylic acids include: acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, oxalic acid, succinic acid, adipic acid, terephthalic acid, 2-bromobutanoic acid, ethyl hydrogen adipate, 4-chlorobenzoic acid, 4-cyanobenzoic acid, 2,3,4,5-tetrachlorobenzoic acid, ethyl hydrogen-o-phthalate, and the like.

The reaction according to this invention is carried out by the catalytic action of a catalyst system consisting essentially of an indium compound, a halide source and an alkali metal compound. The halide component of the catalyst system of this invention can be supplied, at least in part, by the indium compound, the alkali metal compound or a mixture of both. Optionally, a dihalobutene can be included with the catalyst system, as a catalyst adjuvant.

Examples of suitable indium compounds include indium acetate, indium acetylacetonate, indium hydroxide, indium monochloride, indium trichloride, indium oxyhydroxide, indium selenide, indium sulfate, indium tribromide, indium triiodide, indium trioxide and the like and mixtures thereof.

Examples of suitable alkali metal compounds include lithium chloride, lithium bromide, lithium iodide, lithium acetate, lithium benzoate, lithium oxide, lithium octadecanoate, lithium nitrate, sodium chloride, sodium bromide, sodium acetate, sodium nitrate, potassium chloride, potassium acetate, potassium benzoate, potassium nitrate, rubidium chloride, rubidium bromide, rubidium acetate, rubidium nitrate, cesium chloride, cesium acetate, cesium oxide, cesium nitrate, and the like and mixtures thereof.

The third component of the catalyst system of this invention is a source of halide ion, specifically, chloride, bromide or iodide, or mixtures of these ions. As noted above, the halide ion can be supplied, at least in part, by the indium compound, the alkali metal compound, or both. Other halide sources can be employed provided that the cation portion of the halide is substantially inert under the reaction conditions employed according to this invention. Suitable halide sources include the alkaline earth metal halides, such as, for example, magnesium chloride, calcium bromide, magnesium iodide, strontium bromide, barium chloride and the like.

As noted above, it is optional to employ a dihalobutene, such as 1,4-dichloro-2-butene or the corresponding dibromo or diiodo compound, as a catalyst adjuvant. The dihalobutene acts to promote the reaction rate.

The amount of the catalyst system employed in the process of this invention will be expressed in terms of the mole percent of the indium compound based upon the amount of the conjugated diolefin charged to the reaction mixture. The amount of the indium compound will be in the range of about 0.1 to 10, preferably 1 to 3, mole percent of the conjugated diolefin.

The amounts of the alkali metal compound and the halide ion employed in the process of this invention are based upon the indium compound. The molar ratio of the alkali metal compound to the indium compound, and the molar ratio of the halide ion to the indium compound, is in the range of about 0.1:1 to 20:1, preferably about 1:1 to 10:1.

Similarly, when employed, the amount of the dihalobutene catalyst adjuvant is based upon the indium compound. The molar ratio of the dihalobutene to the indium compound is from 0.1:1 to 10:1, preferably in the range of 0.5:1 to 5:1.

The reaction of the instant invention is an oxidation reaction and as such is carried out in the presence of free oxygen. The amount of oxygen present is not believed to be critical though it is recognized that an undesirably slow reaction will result if the concentration of oxygen is very low. Essentially, pure oxygen can be employed as well as mixtures of oxygen with inert gases or air can be employed as a source of free oxygen for the instant reaction. It is recognized that explosive conditions could be obtained if the amount of oxygen added to the reaction system is not under control. The reaction of this invention, as is true with many oxidation reactions, appears to be highly exothermic and this too indicates caution in adding oxygen to the system. Because of these considerations, it is desirable to add the oxygen incrementally or continuously during the reaction to avoid the explosive range of oxygen concentration and to allow better control of the temperature of the reaction. A reaction vessel with efficient mixing means is also desirable to avoid build-up of dangerous concentrations of free oxygen.

The reaction of this invention is carried out at a temperature in the range of 25° C to about 200° C, preferably from about 70° to about 150° C.

The reaction is carried out under an oxygen pressure of from 0.1 to 1000, preferably from 5 to 200, psig of oxygen above autogenous pressure at the temperature employed.

The reaction time ranges from 0.1 to about 12 hours. The reaction time depends upon the temperature, catalyst activity and the oxygen pressure employed.

As described above, the reaction of the instant invention is carried out in the presence of a carboxylic acid which provides the acyl moiety of the final product. It is optional, though presently preferred, to employ, as part of the reaction mixture, the corresponding carboxylic acid anhydride in addition to the carboxylic acid. The use of a carboxylic acid anhydride serves to simplify the purification and separation steps by reducing the amount of by-products which contain free hydroxy groups.

The process of this invention can be carried out in a batch or a continuous fashion.

The process of this invention can be carried out in the liquid phase or in the gas phase.

In a presently preferred embodiment of this invention, the process of this invention is carried out in the liquid phase.

When conducted in the liquid phase, it is preferred that the carboxylic acid employed in the process of this invention be normally liquid or at least liquid under the conditions employed for the reaction. The presently preferred carboxylic acid is acetic acid.

Reaction mixtures obtained according to the process of this invention are generally vented to remove any unreacted oxygen and conjugated diolefin and then distilled to remove the carboxylic acid and anhydride, if present. The product remaining is usually distilled to recover one or more fractions containing the diacyloxy olefins. The catalyst can be recovered from the distillation residue and recycled to the reaction zone as desired. Any unreacted conjugated diolefin recovered from the reaction mixture can also be recycled to the reaction zone as desired. The diacyloxy olefins which are recovered from the product mixture include in many instances an amount of 1,2- or vicinal-isomer which can be recycled to the reaction zone and thereby converted to the desired 1,4-diacyloxy olefin.

The above mentioned 1,4-diacyloxy olefins have utility as intermediates for the preparation of the corresponding saturated diols or tetrahydrofurans. For example, British Pat. No. 1,170,222 describes the ultimate preparation of tetrahydrofurans starting with conjugated diolefins and proceeding through the 1,4-diacyloxy butenes. Tetrahydrofuran itself, of course, would be produced starting with 1,3-butadiene.

The following example illustrates the invention.

EXAMPLE

A 250 ml Fisher-Porter aerosol compatibility bottle equipped with magnetic stirring means was charged with 3.7 grams (10 mmoles) of indium tribromide, 6.5 grams (75 mmoles) of lithium bromide, 4.6 grams (21.5 mmoles) of 1,4-dibromo-2-butene, 50 ml of acetic acid, 25 ml of acetic anhydride, and 11.2 grams (207.4 mmoles) of butadiene in the vapor phase. The reaction vessel was placed in an oil bath and pressured to 30 psig with oxygen and heated to 140° C for 6 hours. During the run, at about 20-minute intervals, the reaction vessel was pressured to 130 psig with oxygen. At the conclusion of the run, the reactor was cooled, vented and the reaction mixture transferred to a distillation vessel wherein the mixture was distilled through an 18 inch Vigreaux column. Two fractions were obtained from the above distillation with fraction 1 having a boiling range of 50°–54° C at 60 millimeters mercury pressure being essentially pure acetic acid as determined by gas-liquid phase chromatography analysis. Fraction 2 boiling at a range of 67°–105° C at 6 millimeters mercury pressure weighed 19.8 grams and was also analyzed by gas-liquid phase chromatography. The analysis of said fraction 2 indicated 4.67 grams (27.2 mmoles) of 1,2-diacetoxy-3-butene, 2.33 grams (13.5 mmoles) of cis-1,4-diacetoxy-2-butene and 5.69 grams (33.1 mmoles) of trans-1,4-diacetoxy-2-butene. A combined yield of 73.8 mmoles of the diacetoxy butenes was thus obtained for a yield of 35.6 percent of said diacetoxy butenes based on starting butadiene charged.

Reasonable variations and modifications, which will be apparent to those skilled in the art, can be made in this invention without departing from the spirit and scope thereof.

What is claimed is:

1. In a process for the production of unsaturated diesters which comprises reacting under reaction conditions a conjugated diolefin with a carboxylic acid by contacting a mixture of said diolefin and said acid with free oxygen wherein the improvements comprises using a catalytic amount of a catalyst system consisting essentially of an indium compound selected from the group consisting of indium acetate, indium acetylacetonate, indium hydroxide, indium monochloride, indium trichloride, indium oxyhydroxide, indium selenide, indium sulfate, indium tribromide, indium triiodide, and indium trioxide, a source of chloride ion, bromide ion or iodide ion or mixture thereof, an alkali metal compound and, optionally, a dihalobutene catalyst adjuvant, wherein the halide moiety of said adjuvant is chloride, bromide or iodide.

2. The process of claim 1 wherein said conjugated diolefin is selected from the group consisting of acyclic conjugated diolefins having from 4 to 16 carbon atoms per molecule represented by the general formula

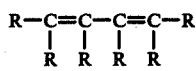

and cyclic conjugated diolefins having from 5 to 16 carbon atoms per molecule represented by the general formula

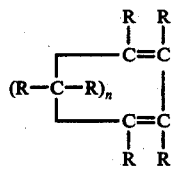

wherein, in each formula, each R is independently selected from the group consisting of hydrogen, halogen, cyano, —COOR′, and alkyl, aryl and cycloalkyl radicals and combinations thereof, of up to 12 carbon atoms per radical, wherein R′ is selected from the group consisting of hydrogen, an alkyl radical of up to 10 carbon atoms and an aryl radical of up to 10 carbon atoms; and wherein $n$ is an integer having a value of 1 to 12.

3. The process of claim 1 wherein said carboxylic acid is selected from the group consisting of monocarboxylic acids having from 2 to 18 carbon atoms per molecule represented by the general formula

and dicarboxylic acids having from 2 to 18 carbon atoms per molecule represented by the general formula

wherein R″ is selected from the group consisting of alkyl, cycloalkyl and aryl radicals and halogen, cyano and —COOR′ substituted derivatives thereof, wherein up to four of said halogen, cyano or —COOR′ substituents can be present in said radical, wherein R′ is selected from the group consisting of hydrogen, an alkyl radical of up to 10 carbon atoms and an aryl radical of up to 10 carbon atoms; and wherein R‴ is selected from the group consisting of a valence bond and alkylene, cycloalkylene and arylene radicals and halogen, cyano and —COOR′ substituted derivatives thereof wherein up to four of said halogen, cyano or —COOR′ substituents can be present in said radical, wherein R′ is as defined above.

4. The process of claim 1 wherein said indium compound is employed in an amount ranging from 0.1 to 10 mole percent, based upon said conjugated diolefin, and each of said halide ion and said alkali metal compound is employed in an amount ranging from 0.1 to 20 moles per mole of said indium compound, and said dihalobutene is employed in an amount of up to about 10 moles per mole of said indium compound.

5. The process of claim 1 wherein said reaction is carried out at a temperature in the range of 25° to about 200° C at an oxygen pressure in the range of 0.1 to 1000 psig above autogenous pressure at the temperature employed.

6. The process of claim 3 wherein there is additionally present a carboxylic acid anhydride corresponding to the carboxylic acid employed.

7. The process of claim 1 wherein said conjugated diolefin is 1,3-butadiene, said carboxylic acid is acetic acid and said catalyst system is indium tribromide and lithium bromide, and said adjuvant is 1,4-dibromo-2-butene.

8. The process of claim 1 wherein said reaction is conducted in the liquid phase.

* * * * *